(12) United States Patent
Nakai et al.

(10) Patent No.: US 7,939,559 B2
(45) Date of Patent: May 10, 2011

(54) LIPASE INHIBITORS

(75) Inventors: Masaaki Nakai, Minoo (JP); Yuko Fukui, Takatsuki (JP); Sumio Asami, Ibaraki (JP); Fumio Hashimoto, Kagoshima (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 158 days.

(21) Appl. No.: 11/631,506

(22) PCT Filed: Jul. 5, 2005

(86) PCT No.: PCT/JP2005/012394
§ 371 (c)(1),
(2), (4) Date: Jan. 4, 2007

(87) PCT Pub. No.: WO2006/004110
PCT Pub. Date: Jan. 12, 2006

(65) Prior Publication Data
US 2008/0207747 A1 Aug. 28, 2008

(30) Foreign Application Priority Data
Jul. 5, 2004 (JP) .................................. 2004-198285

(51) Int. Cl.
*A61K 31/353* (2006.01)
(52) U.S. Cl. ...................................................... 514/456
(58) Field of Classification Search ................. 549/456; 514/456
See application file for complete search history.

(56) References Cited

FOREIGN PATENT DOCUMENTS
EP 0522 502 A1 1/1993
(Continued)

OTHER PUBLICATIONS
Chantr et al, Phytochemistry vol. 9, (2002).*
(Continued)

*Primary Examiner* — Bernard Dentz
(74) *Attorney, Agent, or Firm* — Drinker Biddle & Reath LLP

(57) ABSTRACT

The present invention provides lipase inhibitors containing flavan-3-ol monomers or acylates thereof derived from teas as well as foods and beverages and medicines containing said inhibitors. More specifically, the present invention provides lipase inhibitors containing at least one of flavan-3-ol monomers represented by the formula:

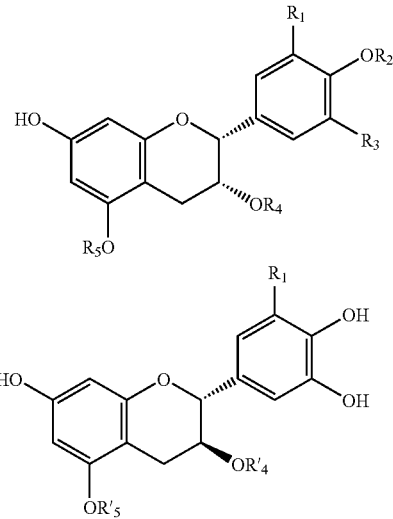

[Formula 1]

wherein $R_1$ and $R_3$ independently represent H or OH, $R_2$ represents H, $R_4$ represents H, G, 3MeG or p-cou, $R_5$ represents H or G, $R_4'$ and $R_5'$ independently represent H or G, $R_4''$ represents H or G, and G, 3MeG and p-cou respectively represent the groups of the formulae:

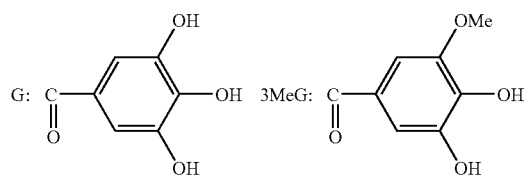

[Formula 2]

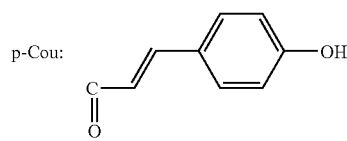

or acylates thereof; as well as foods and beverages and medicines containing said lipase inhibitors.

22 Claims, 1 Drawing Sheet

FOREIGN PATENT DOCUMENTS

| | | | |
|---|---|---|---|
| JP | 60-011912 B | | 2/1983 |
| JP | H01-102022 A | | 4/1989 |
| JP | H2-23929 | * | 2/1990 |
| JP | H03-219872 A | | 9/1991 |
| JP | H03-228664 A | | 10/1991 |
| JP | H07-061927 A | | 3/1995 |
| JP | H08-259557 A | | 10/1996 |
| JP | H09-040689 A | | 2/1997 |
| JP | H09-291039 A | | 11/1997 |
| JP | 2000-226329 | * | 7/1999 |
| JP | 2000-226329 A | | 8/2000 |
| JP | 2002-080362 A | | 3/2002 |
| JP | 2002-104982 A | | 4/2002 |
| JP | 2003-095942 A | | 4/2003 |
| WO | WO 01/80870 A2 | | 11/2001 |

OTHER PUBLICATIONS

International Search Report issued Aug. 16, 2005, in application No. PCT/JP2005/012394, filed Jul. 5, 2005.

Supplementary European Search Report issued Dec. 18, 2009, in European Application No. EP 05 75 8209.0.

Hong et al., "Effects of Tea Polyphenols on Arachidonic Acid Metabolism in Human Colon," in Food Factors in Health Promotion and Disease Prevention, Chapter 4, pp. 27-38, ACS Symposium Series, 200, vol. 851, American Chemical Society.

Yoshikawa et al., "*Salacia reticulata* and its polyphenolic constituents with lipase inhibitory and lipolytic activities have mild antiobesity effects in rats," Journal of Nutrition, 2002, vol. 132, No. 7, pp. 1819-1824.

Kumazawa, "Cha Seibun no Seitaimaku ni Taisuru Shinwasei (1)", Cha, 2001, vol. 54, No. 2, pp. 36-37 (Japanese).

Shimada et al., "Oolong tea increases plasma adiponectin levels and low-density lipoprotein particle size in patients with coronary artery disease," J. Diabetes Research and Clinical Practice, 2004, vol. 65, pp. 227-234.

Chen et al., "Clinical Efficacy of Oolong Tea on Anti-Simple Obesity," Journal of the Japanese Society of Clinical Nutrition, 1998, vol. 20, pp. 83-90 (English translation).

Moreno et al., "Inhibitory Effects of Grape Seed Extract on Lipases," Nutrition, 2003, vol. 19, pp. 876-879.

Matsuda et al., "Effects of crude drugs on experimental hypercholesterolemia. I. Tea and its active principles," Journal of Ethnopharmacology, Sep. 1986, vol. 17, No. 3, pp. 213-224.

Hashimoto et al., "Tannins and Related Compounds, XC,[11] 8-$C$-Ascorbyl (−)-Epigallocatechin 3-$O$-Gallate and Novel Dimeric Flavan-3-ols, Oolonghomobisflavans A and B, from Oolong Tea," Chem. Pharm. Bull, 1989, vol. 37, No. 12, pp. 3255-3263.

Hashimoto et al., "Evaluation of the Anti-oxidative Effect (in vitro) of Tea Polyphenols," Biosci. Biotechnol. Biochem., 2003, No. 67, vol. 2, pp. 396-401.

Mittal et al., "Dietary feeding of proanthocyanidins from grape seeds prevents photocarcinogenesis in SKH-1 hairless mice: relationship to decreased fat and lipid peroxidation," Carcinogenesis, 2003, vol. 34, No. 8, pp. 1379-1388.

Nakai et al., "Inhibitory Effects of Oolong Tea Polyphenols on Pancreatic Lipase In Vitro," Journal of Agricultural and Food Chemistry, 2005, vol. 53, pp. 4593-4598.

Han et al., "Anti-obesity action of oolong tea," Int. J. Obes. Relat. Metab. Disord., Apr. 27, 1998, vol. 23, pp. 98-105.

Iwata et al., "Effect of Oolong Tea on Plasma Lipids and Lipoprotein Lipase Activity in Young Women," J. Jpn. Soc. Nutr. Food Sci., 1991, vol. 44, No. 4, pp. 251-259 (English Translation).

Hashimoto et al., "Tannins and Related Compounds. LVI. Isolation of Four New Acylated Flavan-3-ols from Oolong Tea. (1)," Chem. Pharm. Bull, 1987, vol. 35, No. 2, pp. 611-616.

* cited by examiner

Figure 1  Chemical Structural Formulae of the Test Samples evaluated for Lipase Inhibitory Activity
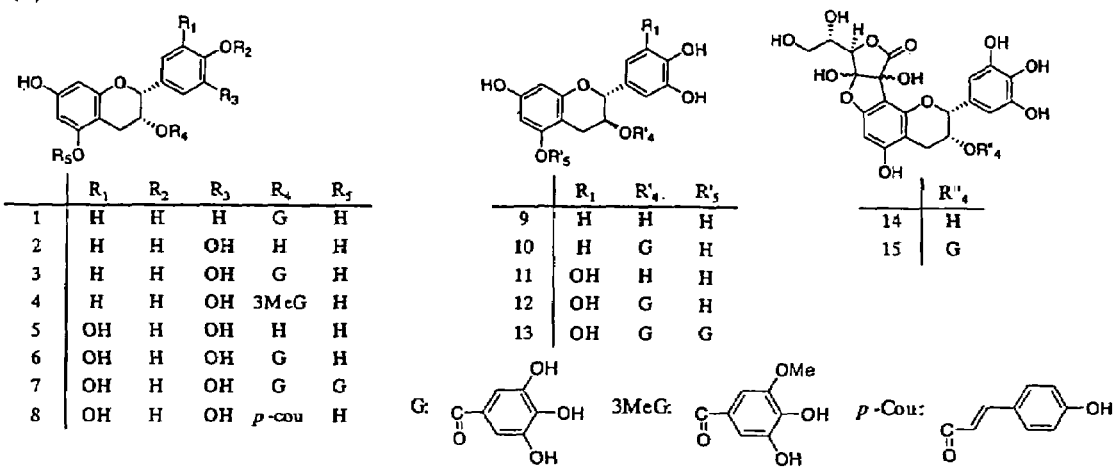

LIPASE INHIBITORS

CROSS REFERENCE TO RELATED APPLICATIONS

This application is a National Stage of International Application No. PCT/JP2005/012394 filed Jul. 5, 2005, and which claims benefit of Japanese Patent Application No. 2004-198285 filed Jul. 5, 2004, and are incorporated by reference herein in their entirety.

TECHNICAL FIELD

The present invention provides lipase inhibitors containing flavan-3-ol monomers or acylates thereof derived from teas.

BACKGROUND ART

In recent years, intake of high-fat foods in Japanese people has been increasing with the increasing westernization of their life style. The 1999 National Nutrition Survey reports that the fat energy ratio exceeds the proper level of 25% despite of the energy intake decreasing year by year and that 50 to 60 percent of the 60 and older population has high triglyceride levels or high cholesterol levels (Ministry of Health, Labor and Welfare of Japan. An overview of the results of the 1999 National Nutrition Survey. Japanese Journal of Clinical Nutrition 2001; 98(5): 577-588).

Obesity is one of the most important diseases in modern society, and mainly caused by excessive consumption of fats. Excessive consumption of fats is known to induce not only obesity but also obesity-associated conditions such as diabetes, hyperlipemia, hypertension and arteriosclerosis. An appetite suppressant Mazindol® is the only drug approved for this obesity in Japan, but it was reported to have adverse side effects such as dry mouth, constipation, stomach discomfort and nausea/vomiting (Clinical Evaluation 1985; 13(2): 419-459; Clinical Evaluation 1985; 13(2): 461-515). Outside Japan, a commercially available drug for improving obesity is Xenical®, which functions to suppress intestinal fat absorption by lipase inhibitory activity, but it is not always safe because it was also reported to have adverse side effects such as fatty stools, increased stool frequency, loose stools, diarrhea and abdominal pain (Lancet 1998; 352: 67-172).

An effective means to prevent obesity is to reduce caloric intake by dietary restrictions, but they should be supervised by an experienced nutrition counselor and it is often difficult to follow them in daily life. Thus, a safe and healthful way to inhibit the absorption of dietary fats by the body would be a practical and useful approach to the treatment of obesity and related diseases or health enhancement.

Against this background, attention has been given to the development of foods for specified health use with proven safety and effectiveness for humans. Foods for specified health use so far marketed as food materials for controlling the increase in serum triglyceride levels after eating include globin digests suppressing fat absorption by pancreatic lipase inhibition (J. Nutr. 1998; 128: 56-60; Journal of the Japanese Society of Nutrition and Food Science 1999; 52(2): 71-77; Journal of Health Food & Nutrition Food Studies 2002; 5(3): 131-144); diacylglycerols having different digestion/absorption characteristics from those of triacylglycerols (J. Am. Coll. Nutr. 2000; 19(6): 789-796; Clin. Chim. Acta. 2001; 11(2): 109-117); and eicosapentaenoic acid (EPA) and docosahexaenoic acid (DHA) purified from fish oils, etc.

Attention is also recently being given to plant-derived materials having lipase inhibitory activity, and especially various polyphenols having lipase inhibitory activity have been reported, such as plant bark-derived tannin (Japanese Patent Publication Sho 60-11912); tannins and flavonoids and glycosides thereof contained in a legume *Cassia nomame* (Japanese Patent Laying Open Hei 8-259557); food products for inhibiting lipid absorption containing epigallocatechin gallate and epicatechin gallate known as major ingredients in green tea (Japanese Patent Laying Open Hei 3-228664); lipase inhibitors comprising aqueous extracts of green pepper, shimeji mushroom, pumpkin, maitake mushroom, hijiki seaweed, green tea, oolong tea, etc. (Japanese Patent Laying Open Hei 3-219872); flavones and flavonols (Japanese Patent Laying Open Hei 7-61927); hydroxybenzoic acids (gallic acid) (Japanese Patent Laying Open Hei 1-102022); triterpene compounds and derivatives thereof (Japanese Patent Laying Open Hei 9-40689); anti-obesity agents containing procyanidin from tamarind as an active ingredient (Japanese Patent Laying Open Hei 9-291039); as well as lipase inhibitory effects of grape seed extracts (Nutrition 2003; 19(10): 876-879); lipase inhibitory effects and anti-obesity effects in rats of Salacia-derived polyphenols (J. Nutr. 2002; 132: 1819-1824); and anti-obesity effects of oolong tea extracts in mice (Int. J. Obes. 1999; 23: 98-105).

However, plant-derived lipase inhibitors so far reported as shown above are not sufficiently effective. Even if an extract of a plant was effective, for example, it would be difficult to stably maintain lipase inhibitory activity unless the amount of the active ingredient contained in it is specified because it is naturally derived. Moreover, inhibitors derived from tasteless plants have the disadvantage that they affect flavor when they are used as foods or beverages. For example, there are several reports showing the effect of oolong tea in improving lipid profiles by demonstrating a significant decrease in blood triglyceride levels after drinking 1330 ml of commercially available oolong tea daily for 6 weeks (Journal of the Japanese Society of Nutrition and Food Science 1991; 44(4): 251-259) or a weight loss of 1 kg or more in 67% of subjects consisting of 102 men and women with simple obesity who continuously took oolong tea (2 g×4/day) orally for 6 weeks and a significant improving effect after ingestion of oolong tea in subjects showing high blood triglyceride levels (Journal of the Japanese Society of Clinical Nutrition 1998; 20(1): 83-90). Thus, beneficial effects have been observed by drinking plenty of oolong tea, but it is difficult to continue to do so in daily life. If simply concentrated oolong tea was provided, it would not be suitable as a practical means because of strong bitterness/astringency and high caffeine content.

Patent Documents
1. Japanese Patent Publication Sho 60-11912
2. Japanese Patent Laying Open Hei 8-259557
3. Japanese Patent Laying Open Hei 3-228664
4. Japanese Patent Laying Open Hei 3-219872
5. Japanese Patent Laying Open Hei 7-61927
6. Japanese Patent Laying Open Hei 1-102022
7. Japanese Patent Laying Open Hei 9-40689
8. Japanese Patent Laying Open Hei 9-291039

Non-Patent Documents
1. Ministry of Health, Labor and Welfare of Japan. An overview of the results of the 1999 National Nutrition Survey.
2. Japanese Journal of Clinical Nutrition 2001; 98(5): 577-588.
3. Clinical Evaluation 1985; 13(2): 419-459. Clinical Evaluation 1985; 13(2): 461-515.
4. Lancet 1998; 352: 67-172.
5. J. Nutr. 1998; 128: 56-60.
6. Journal of the Japanese Society of Nutrition and Food Science 1999; 52(2): 71-77.

7. Journal of Health Food & Nutrition Food Studies 2002; 5(3): 131-144.
8. J. Am. Coll. Nutr. 2000; 19(6): 789-796.
9. Clin. Chim. Acta. 2001; 11(2): 109-117.
10. Nutrition 2003; 19(10): 876-879.
11. J. Nutr. 2002; 132: 1819-1824.
12. Int. J. Obes. 1999; 23: 98-105.
13. Journal of the Japanese Society of Nutrition and Food Science 1991; 44(4): 251-259.
14. Journal of the Japanese Society of Clinical Nutrition 1998; 20(1): 83-90.
15. Chem. Pharm. Bull 1987; 35(2): 611-616.
16. Chem. Pharm. Bull 1989; 37(12): 3255-3563.

DISCLOSURE OF THE INVENTION

Problem to be Solved by the Invention

The present invention focuses on ingredients contained in highly tasty teas and provides lipase inhibitors containing at least one of flavan-3-ol monomers or acylates thereof derived from teas.

The present invention also provides highly tasty foods and beverages containing said lipase inhibitors for reducing blood triglycerides and for enhancing health.

The present invention also provides pharmaceutical compositions containing said lipase inhibitors for inhibiting absorption of dietary fats to prevent an increase in blood triglycerides.

Means for Solving Problem

As a means for solving the above problems, we found tea-derived ingredients inhibiting pancreatic lipase essential for fat absorption, and evaluated the lipase inhibitory activity of various polyphenols present therein, and ascertained that flavan-3-ol monomers or acylates thereof have strong lipase inhibitory activity.

More specifically, lipase inhibitors of the present invention are characterized in that they contain at least one of flavan-3-ol monomers represented by the formula:

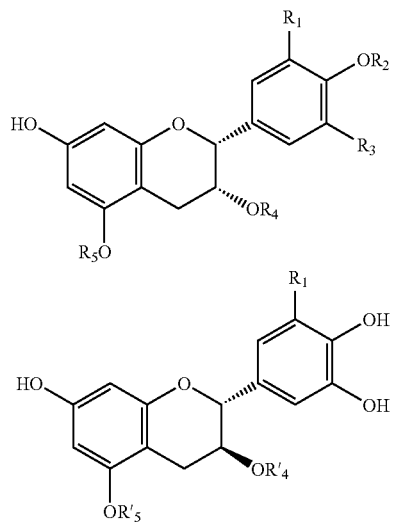

or

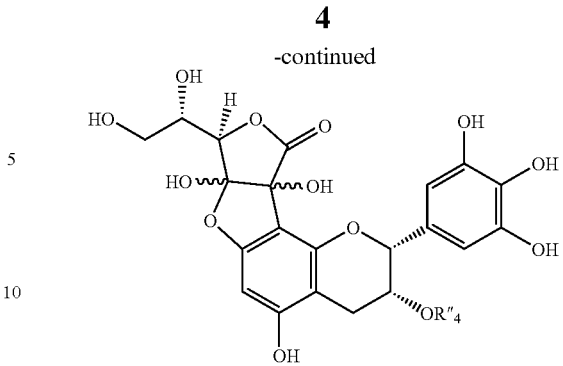

wherein $R_1$ and $R_3$ independently represent H or OH, $R_2$ represents H, $R_4$ represents H, G, 3MeG or p-cou, $R_5$ represents H or G, $R_4'$ and $R_5'$ independently represent H or G, $R_4''$ represents H or G, and G, 3MeG and p-cou respectively represent the groups of the formulae:

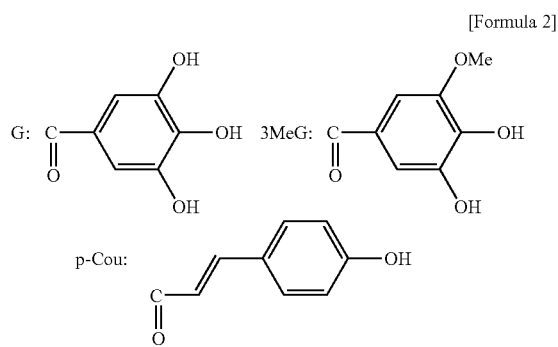

or acylates thereof.

Preferred flavan-3-ol monomers or acylates thereof are selected from the group consisting of (−)-epiafzelechin 3-O-gallate (compound 1), (−)-epicatechin 3-O-gallate (compound 3), (−)-epicatechin 3-O-(3'-O-methyl-gallate) (compound 4), (−)-epigallocatechin 3-O-gallate (compound 6), (−)-epigallocatechin 3,5-di-O-gallate (compound 7), (−)-epigallocatechin 3-O-p-coumaroate (compound 8), (−)-catechin 3-O-gallate (compound 10), (−)-gallocatechin 3-O-gallate (compound 12), gallocatechin 3,5-di-O-gallate (compound 13), 8-C-ascorbyl-(−)-epigallocatechin (compound 14), and 8-C-ascorbyl-(−)-epigallocatechin 3-O-gallate (compound 15). Especially preferred is (−)-epigallocatechin 3,5-di-O-gallate (compound 7) in terms of high lipase inhibitory activity.

Flavan-3-ol monomers or acylates thereof of the present invention are commercially available or can be obtained by extraction from natural materials such as commercially available green tea, black tea and oolong tea. For example, purification of flavan-3-ol ingredients from oolong tea leaves is reported in Chem. Pharm. Bull. 1987; 35(2): 611-616 or Chem. Pharm. Bull. 1989; 37(12): 3255-3563, and the presence of various catechins and acylates thereof has been identified. Gallocatechin 3,5-di-O-gallate can be obtained as described in Example 2 below.

Lipase Inhibitors

Flavan-3-ol monomers or acylates thereof of the present invention can be used alone as lipase inhibitors without including other components, or can be used as lipase inhibitors in combination with solvents or solid carriers. The solvents or carriers are preferably those capable of being safely used as foods or medicines in terms of the uses for foods and beverages and/or medicines as described below. Lipase inhibitors of the present invention have various uses such as experimental and research purposes or uses as active ingredients of foods and medicines for preventing accumulation of triglycerides.

Method for Assaying Lipase Inhibitory Activity

Lipase inhibitors of the present invention have a strong inhibitory effect against lipases, especially pancreatic lipase. The inhibitory activity can be assayed by the method specifically described in Example 1.

Foods and Beverages Containing Lipase Inhibitors

Lipase inhibitors containing flavan-3-ol monomers or acylates thereof of the present invention can be added as active ingredients for inhibiting lipase to foods and beverages to prevent an undesirable increase in blood triglycerides associated with intake of dietary fats and/or reduce increased blood triglycerides. Preferred examples of foods and beverages include those consumed on a daily basis such as green tea, barley tea, oolong tea, black tea, coffee, isotonic drink, drinking water, seasonings, and dressings. However, the foods and beverages may be those commonly consumed such as soft drinks, cocktails, beer, whiskey, distilled spirits, wine, sake, seasonings, dressings, flavored rice, processed foods, convenience foods, retort foods, chocolates, fresh cream, cakes, dairy products, health foods and supplements.

Lipase inhibitors of the present invention are added to foods and beverages in an amount corresponding to an intake of flavan-3-ol monomers or acylates thereof of 0.1 mg to 10 g per meal. However, there is no substantial upper limit on the amount of flavan-3-ol monomers or acylates thereof of the present invention that can be added to foods and beverages because they are derived from foods and therefore very safe.

Medicines Containing Lipase Inhibitors

Lipase inhibitors containing flavan-3-ol monomers or acylates thereof of the present invention can also be used as active ingredients of drugs for inhibiting absorption of dietary fats and preventing and/or reducing an undesirable increase of blood triglycerides. Preferred drugs are those orally administered, such as drinkable preparations, tablets, capsules, granules, powders, candies and hard candies. The amount of compounds of the present invention is 0.1 mg to 10 g per dose.

Medicines of the present invention are safely taken even for a long period because of high safety of lipase inhibitor ingredients. Therefore, they can be taken even on a daily basis to prevent or correct obesity as a lifestyle-related disease.

Effect of the Invention

The present invention can provide highly tasty foods and beverages containing a lipase inhibitor including at least one of flavan-3-ol monomers or acylates thereof derived from tea leaves for reducing triglycerides and for enhancing health without compromising flavor. Beverages enriched with tea-derived active ingredients are very significant because the inhibitor should desirably be taken with meals in order to inhibit absorption of dietary fats. Especially, the present invention made it possible to develop teas capable of reducing triglycerides by enriching them with these ingredients.

BRIEF EXPLANATION OF THE DRAWINGS

FIG. 1 shows the chemical structural formulae of the compounds evaluated for lipase inhibitory activity in Example 3.

EXAMPLES

Examples 1

Lipase Inhibitory Activity Assay

A lipase activity assay was performed by using the oleate ester of fluorescent 4-methylumbelliferone (4-MUO) as a substrate to measure the fluorescence of 4-methylumbelliferone produced by reaction.

The buffer used for the assay was 13 mM Tris-HCl (pH 8.0) containing 150 mM NaCl, 1.36 mM $CaCl_2$. The enzyme assay was performed using a 0.1 M solution of the substrate 4-MUO (Sigma) in DMSO diluted 1:1000 in said buffer and a solution of porcine pancreatic lipase (Sigma) prepared at 400 U/ml also in said buffer.

An enzymatic reaction was started by adding 25 µl of the lipase/buffer solution after 50 µl of the 4-MUO/buffer solution and 25 µl of distilled water (or an aqueous solution of each sample) were added and mixed in a 96-well microplate at 25° C. After the reaction was performed for 30 minutes, the reaction was stopped by adding 100 µl of a 0.1 M citrate buffer (pH 4.2) and the fluorescence of 4-methylumbelliferone produced by the reaction (excitation 355 nm, emission 460 nm) was measured using a fluorescence plate reader (Fluoroskan Asent CF from Labsystems).

The inhibitory activity of each test sample was determined as $IC_{50}(\mu M)$, i.e. the amount of the sample giving 50% inhibition of the activity of the control (distilled water).

Test Samples (−)-Epicatechin (compound 2), (−)-epicatechin 3-O-gallate (compound 3), (−)-epigallocatechin (compound 5), (−)-epigallocatechin 3-O-gallate (compound 6), (+)-catechin (compound 9), (−)-catechin 3-O-gallate (compound 10), (+)-gallocatechin (compound 11) and (−)-gallocatechin 3-O-gallate (compound 12) were purchased from Wako Pure Chemical Industries, Ltd.

(−)-Epiafzelechin 3-O-gallate (compound 1), (−)-epicatechin 3-0-(3'-O-methyl-gallate) (compound 4), (−)-epigallocatechin 3,5-di-O-gallate (compound 7) and (−)-epigallocatechin 3-O-p-coumaroate (compound 8) were isolated according to Chem. Pharm. Bull 35 (2), 611-616 (1987), and 8-C-ascorbyl-(−)-epigallocatechin (compound 14) and 8-C-ascorbyl-(−)-epigallocatechin 3-O-gallate (compound 15) were isolated according to the article Chem. Pharm. Bull 37 (12), 3255-3563 (1989). Gallocatechin 3,5-di-O-gallate (compound 13) was purified by the method of Example 2.

Example 2

Leaves of Camellia ptilophylla (0.100 g) (dry matter) were extracted with 2000 ml of hot water (90° C.) for 4 min and lyophilized. The lyophilized material was purified as follows. A 1% aqueous solution of the lyophilized powder was adsorbed to Sep-Pak C18 Cartridge (5 ml, Waters) and washed with water, after which a fraction eluted with acetonitrile was lyophilized. This fraction (250 mg) was applied onto Develosil C30-UG-5 (20 mm×250 mm, Nomura Chemical Co., Ltd.) and eluted with a linear gradient of 5-30% acetonitrile in the presence of 0.05% TFA (5 ml/min, 180 min) and fractionated while monitoring the absorbance at 280 nm. The subfraction obtained was then applied onto YMC-Pak ODS (20×250 mm, YMC Co., Ltd.) and purified by elution with a linear gradient of 20-25% acetonitrile in the presence of 0.1% TFA (6 ml/mim, 60 min) to give gallocatechin 3,5-di-O-gallate (13).

Example 3

Lipase Inhibitory Activity of Catechins

Lipase inhibitory activities of catechins and acylated catechins are shown in Table 1. The chemical structural formulae of the compounds subjected to evaluation are shown in FIG. 1.

[Table 1]

TABLE 1

| compound | IC$_{50}$ (µM) |
|---|---|
| Flavan-3-ols | |
| (−)-epiafzelechin 3-O-gallate (1) | 2.582 |
| (−)-epicatechin (2) | >20 |
| (−)-epicatechin 3-O-gallate (3) | 0.452 |
| (−)-epicatechin 3-O-(3′-O-methyl-gallate) (4) | 0.680 |
| (−)-epigallocatechin (5) | >20 |
| (−)-epigallocatechin 3-O-gallate (6) | 0.349 |
| (−)-epigallocatechin 3,5-di-O-gallate (7) | 0.098 |
| (−)-epigallocatechin 3-O-p-coumaroate (8) | 0.885 |
| (+)-catechin (9) | >20 |
| (−)-catechin 3-O-gallate (10) | 0.543 |
| (+)-gallocatechin (11) | >20 |
| (−)-gallocatechin 3-O-gallate (12) | 0.437 |
| (−)-gallocatechin 3,5-di-O-gallate (13) | 0.213 |
| 8-C-ascorbyl(−)-epigallocatechin (14) | 0.646 |
| 8-C-ascorbyl(−)-epigallocatechin 3-O-gallate (15) | 0.791 |

Among major catechins (8 catechins corresponding to compounds 2, 3, 5, 6, 9, 10, 11, 12) present in teas, four flavan-3-ols having a gallate moiety bonded via an ester linkage (compounds 3, 6, 10, 12) showed lipase inhibitory activity. Especially, (−)-epigallocatechin 3-O-gallate (EGCG: 6) most abundantly found in tea leaves showed the strongest activity among these catechins. (−)-Epigallocatechin 3,5-di-O-gallate (7) having an additional gallate molecule attached to EGCG showed an activity about 3.5 times higher than that of EGCG, and gallocatechin 3,5-di-O-gallate (13) having an additional gallate molecule attached to (−)-gallocatechin 3-O-gallate (GCG: 12) showed an activity about twice higher than that of GCG. Compounds having no gallate group in their molecule such as (+)-catechin did not show lipase inhibitory activity and the activity increased with the number of gallate groups, demonstrating that the presence of a gallate group in the molecule is required for producing activity.

The invention claimed is:

1. A method for suppressing absorption of dietary lipids and/or suppressing a rise of triglycerides in blood in a mammal comprising administering to the mammal a composition consisting essentially of at least one of the compounds represented by the formula:

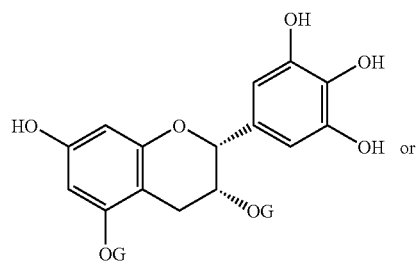

or

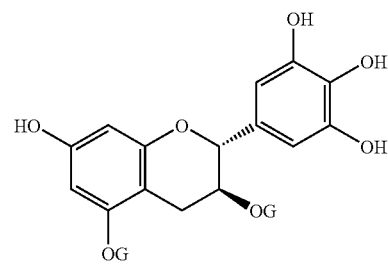

wherein G is represented by the formula:

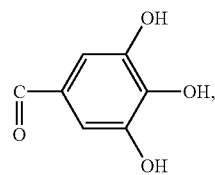

wherein the compound(s) is administered in a total amount effective to suppress absorption of dietary lipids and/or suppress a rise of triglycerides in blood in the mammal, and wherein the composition suppresses absorption of dietary lipids and/or suppresses a rise of triglycerides in blood in the mammal.

2. The method of claim 1, wherein the composition containing at least (−)-epigallocatechin 3,5-di-O-gallate.

3. The method of claim 1 or 2, wherein the composition contains at least one of the compounds in an amount of 0.1 mg or more per meal or 0.1 mg or more per dose.

4. The method of claim 3, wherein the composition contains at least one of the compounds in an amount of 0.1 mg to 10 g per meal or 0.1 mg to 10 g per dose.

5. The method of claim 4, wherein the composition is a food or beverage, or a pharmaceutical composition.

6. The method of claim 5, wherein the composition is a food or beverage selected from the group consisting of tea drinks, soft drinks and health foods.

7. A method for inhibiting lipase activity in a mammal comprising administering to the mammal a composition consisting essentially of at least one of the compounds represented by the formula:

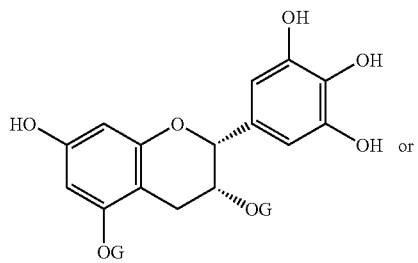

or

-continued

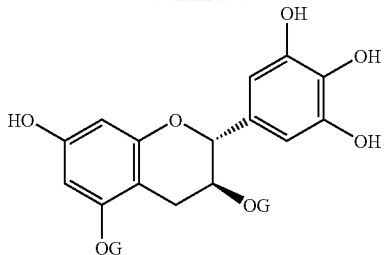

wherein G is represented by the formula:

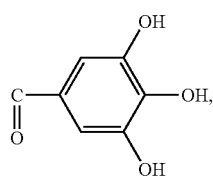

wherein the compound(s) is administered in a total amount effective to inhibit lipase activity in the mammal, and wherein the composition inhibits lipase activity in the mammal.

8. The method of claim 7, wherein the method comprises using at least (−)-epigallocatechin 3,5-di-O-gallate.

9. A method for treating a disease or condition ameliorated by administering a lipase inhibitory agent in a mammal comprising administering to the mammal a composition consisting essentially of at least one of the compounds represented by the formula:

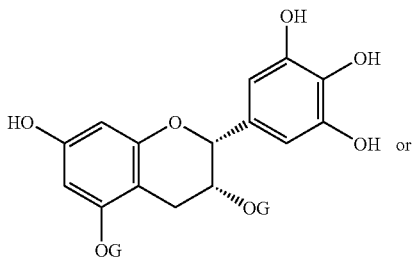

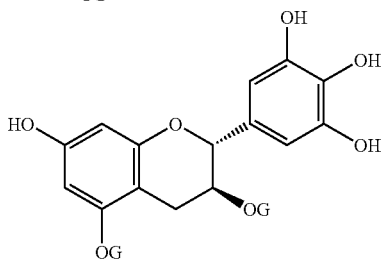

wherein G is represented by the formula:

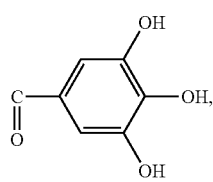

wherein the compound(s) is administered in a total amount effective to treat the disease or condition in the mammal, and wherein the disease or condition ameliorated by administering a lipase inhibitory agent is treated with the composition.

10. The method of claim 9, wherein the composition containing at least (−)-epigallocatechin 3,5-di-O-gallate.

11. The method of claim 9 or 10, wherein the disease or condition is one selected from the group consisting of obesity, diabetes, hyperlipidemia, hypertension, arteriosclerosis and hypertriglyceridemia.

12. A method of producing a food or beverage comprising using, as an ingredient in the food or beverage, a composition consisting essentially of at least one of the compounds represented by the formula:

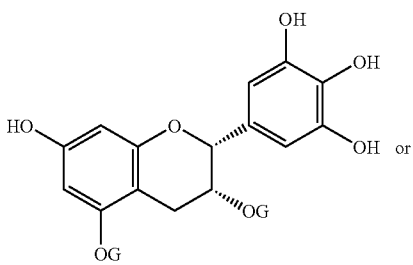

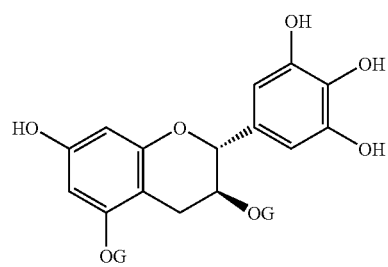

wherein G is represented by the formula:

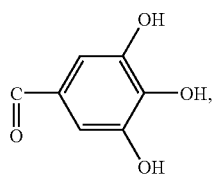

and wherein the compound(s) is included in a total amount effective to suppress absorption of dietary lipids and/or suppress a rise of triglycerides in blood in a mammal, thereby obtaining the food or beverage that has an ability to suppress absorption of dietary lipids and/or suppress a rise of triglycerides in blood in the mammal.

13. A method for suppressing absorption of dietary lipids and/or suppressing a rise of triglycerides in blood in a mammal comprising administering to the mammal at least one of the compounds represented by the formula:

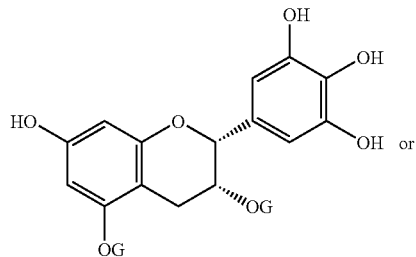

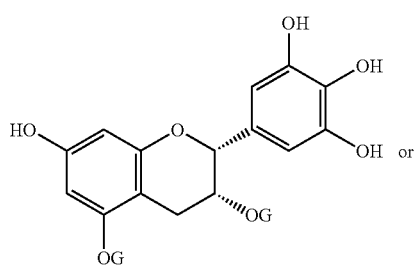

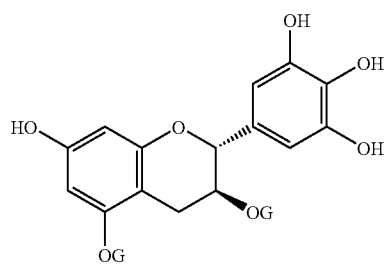

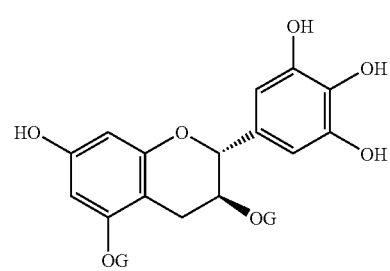

wherein G is represented by the formula:

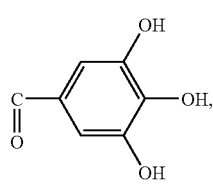

and wherein the compound(s) suppresses absorption of dietary lipids and/or suppresses a rise of triglycerides in the blood in the mammal.

14. The method of claim 13, wherein the method comprises administering at least at least (−)-epigallocatechin 3,5-di-O-gallate.

15. The method of claim 13 or 14, wherein the method comprises administering at least one of the compounds in an amount of 0.1 mg or more per meal or 0.1 mg or more per dose.

16. The method of claim 15, wherein the method comprises administering at least one of the compounds in an amount of 0.1 mg to 10 g per meal or 0.1 mg to 10 g per dose.

17. The method of claim 13, wherein at least one of the compounds is included in a food, a beverage, or a pharmaceutical composition.

18. The method of claim 17, wherein the food or beverage is selected from the group consisting of tea drinks, soft drinks, and health foods.

19. A method for inhibiting lipase activity in a mammal comprising administering to the mammal at least one of the compounds represented by the formula:

wherein G is represented by the formula:

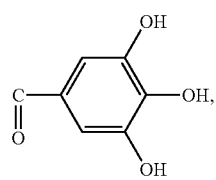

and wherein the compound(s) inhibits lipase activity in the mammal.

20. A method for treating a disease or condition ameliorated by administering a lipase inhibitory agent in a mammal comprising administering to the mammal at least one of the compounds represented by the formula:

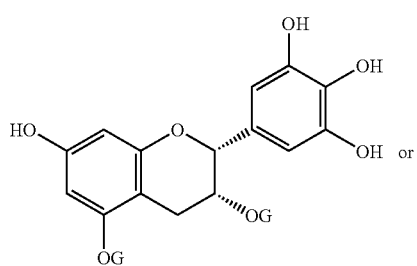

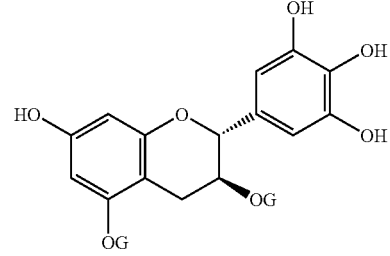

wherein G is represented by the formula:

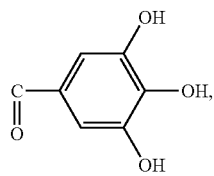

and wherein the disease or condition ameliorated by administering the lipase inhibitory agent is treated with the compound(s).

21. The method of claim 20, wherein the disease or condition is one selected from the group consisting of obesity, diabetes, hyperlipidemia, hypertension, arteriosclerosis, and hypertriglyceridemia.

22. A method for suppressing absorption of dietary lipids and/or suppressing a rise of triglycerides in blood in a mammal in need thereof comprising administering to the mammal at least one of the compounds represented by the formula:

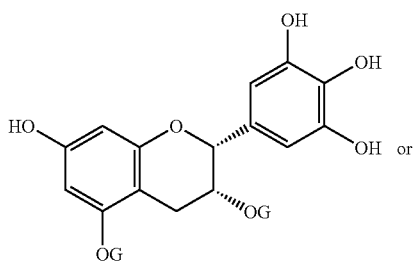 or

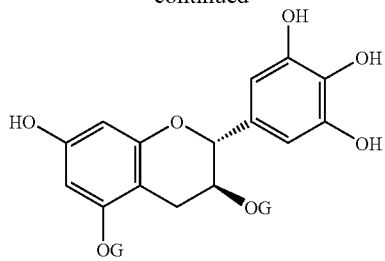

wherein G is represented by the formula:

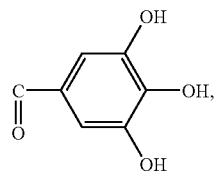

and wherein the compound(s) suppresses absorption of dietary lipids and/or suppresses a rise of triglycerides in the blood in the mammal.

* * * * *